United States Patent [19]
Boje et al.

[11] Patent Number: 6,068,437
[45] Date of Patent: May 30, 2000

[54] AUTOMATED LABORATORY SPECIMEN ORGANIZER AND STORAGE UNIT

[75] Inventors: John F. Boje, Omaha; Samuel R. Brown, Bellevue; Rodney S. Markin, Omaha, all of Nebr.

[73] Assignee: Lab-Interlink, Omaha, Nebr.

[21] Appl. No.: 09/198,636

[22] Filed: Nov. 24, 1998

[51] Int. Cl.[7] .......................... B65G 1/127; B65G 1/137; B01L 9/06
[52] U.S. Cl. ................. 414/331.02; 198/465.1; 198/346.2; 198/347.3
[58] Field of Search .................. 414/331.01, 331.02, 414/331.03, 331.04, 751.1; 198/465.1, 346.2, 347.3

[56] References Cited

U.S. PATENT DOCUMENTS

| | | | |
|---|---|---|---|
| 5,233,844 | 8/1993 | Knippscheer et al. | 414/331.05 X |
| 5,417,922 | 5/1995 | Markin et al. | 422/65 |
| 5,529,166 | 6/1996 | Markin et al. | 198/349 |
| 5,589,137 | 12/1996 | Markin et al. | 422/104 |
| 5,735,387 | 4/1998 | Polaniec et al. | 198/690.1 |
| 5,941,366 | 8/1999 | Quinlan et al. | 198/465.1 |
| 6,010,016 | 1/2000 | Siegal | 211/126 |

*Primary Examiner*—Robert P. Olszewski
*Assistant Examiner*—Gerald J. O'Connor
*Attorney, Agent, or Firm*—Koley Jessen P.C. A Limited Liability Organization; Mark D. Frederiksen

[57] ABSTRACT

A laboratory organizer unit includes an enclosed housing with a storage area containing a plurality of racks for storing specimen containers, the racks movable throughout the storage area to permit access to all of the racks from an opening in the upper end of the storage area. A robotic transfer apparatus is operable to insert and retrieve specimen containers from selected racks in the storage area and move them between the storage area and a buffer area on the housing, as well as between the buffer area and a conveyor located adjacent the housing. The conveyor is of a type which transports specimen carriers having a specimen container therein, and the buffer area includes a rack for intermediate storage of specimen containers. The buffer area thereby permits the transfer apparatus to retrieve and load specimen containers on specimen carriers on the conveyor, while awaiting an appropriate rack to move into position in the storage area.

17 Claims, 5 Drawing Sheets

AUTOMATED LABORATORY SPECIMEN ORGANIZER AND STORAGE UNIT

TECHNICAL FIELD

The present invention relates generally to storage units for clinical laboratory containers, and more particularly to an improved laboratory organizer for storing, organizing and manipulating laboratory containers.

BACKGROUND OF THE INVENTION

Clinical laboratory testing has changed and improved remarkably over the past several years. Initially, tests or assays were performed manually, and generally utilized large quantities of serum, blood or other materials and/or body fluids. As mechanical technology developed in the industrial work place, similar technology was introduced into the clinical laboratory. With the introduction of new technology, methodologies were also improved in an effort to improve the quality of the results produced by the individual instruments, and to minimize the amount of specimen required to perform each test.

More recently, instruments have been developed to increase the efficiency of testing procedures by reducing turnaround time and decreasing the volumes necessary to perform various assays. Present directions in laboratory testing focus on cost containment procedures and instrumentation. Robotic engineering has evolved to such a degree that various types of robots and conveyance systems have been effectively applied in the clinical laboratory setting, permitting the substantial automation of the laboratory.

With the advent of laboratory automation systems, a variety of accessories and associated equipment must also be developed. In this regard, the insertion and retrieval of specimens on to a conveyor track of a laboratory automation system have been slow and ineffective. In addition, prior art laboratory automation systems suffered from difficulties in organizing specimen containers, manipulation of the specimen containers as well as short term and long term storage of the specimen containers.

SUMMARY OF THE INVENTION

It is therefore a general object of the present invention to provide an improved laboratory organization unit for effective storage of specimen containers from a laboratory automation system.

Another object is to provide a laboratory organizer unit which permits quick and efficient insertion and retrieval of specimen containers from a conveyor track.

Still another object of the present invention is to provide an organizer unit which permits efficient short term and long term storage of specimen containers, while permitting effective organization and sorting of the containers in the storage unit.

These and other objects will be apparent to those skilled in the art.

The laboratory organizer unit of the present invention includes an enclosed housing with a storage area containing a plurality of racks for storing specimen containers, the racks movable throughout the storage area to permit access to all of the racks from an opening in the upper end of the storage area. A robotic transfer apparatus is operable to insert and retrieve specimen containers from selected racks in the storage area and move them between the storage area and a buffer area on the housing, as well as between the buffer area and a conveyor located adjacent the housing. The conveyor is of a type which transports specimen carriers having a specimen container therein, and the buffer area includes a rack for intermediate storage of specimen containers. The buffer area thereby permits the transfer apparatus to retrieve and load specimen containers on specimen carriers on the conveyor, while awaiting an appropriate rack to move into position in the storage area.

DESCRIPTION OF THE PREFERRED EMBODIMENT

Figure 1:
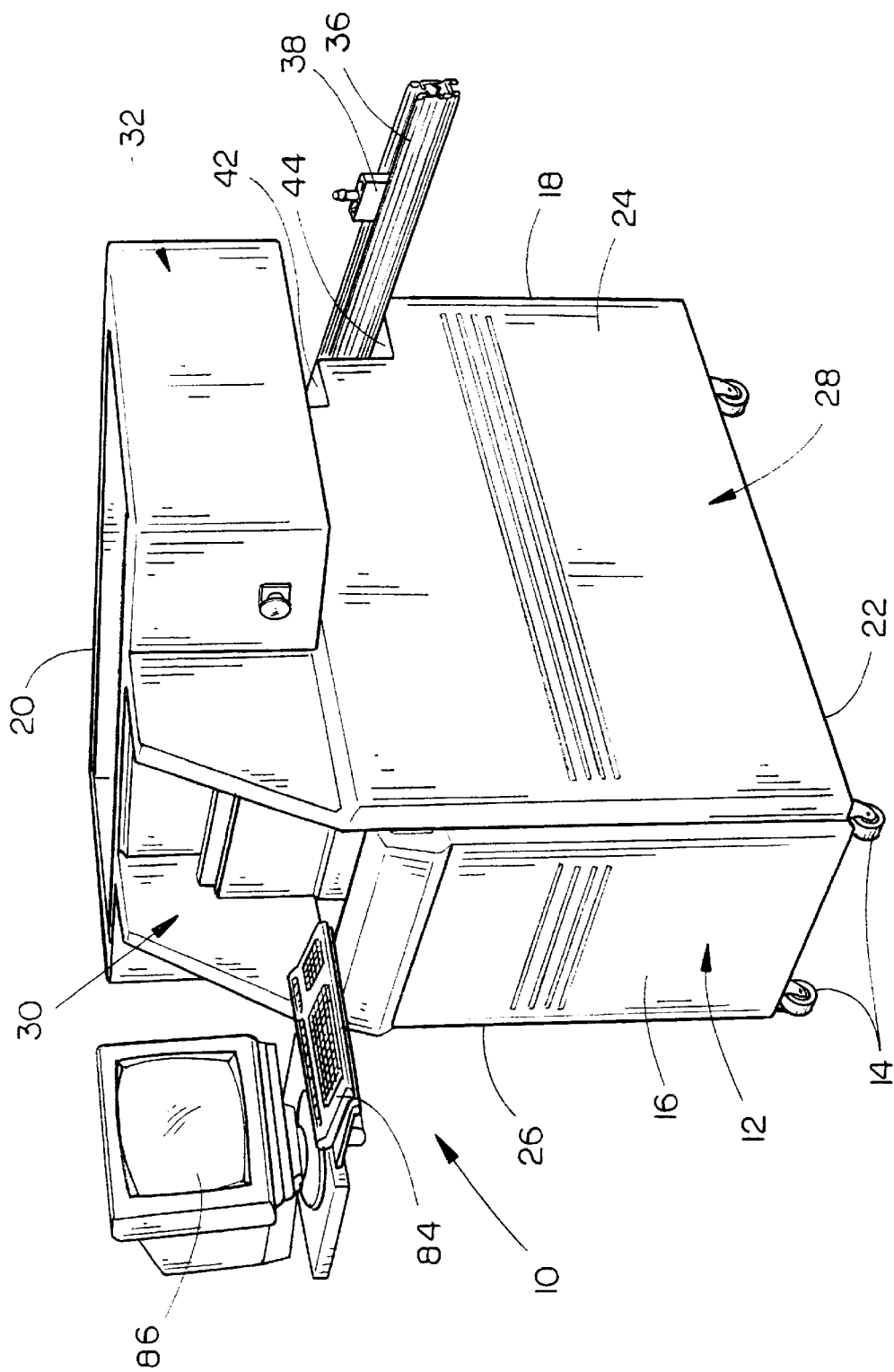
FIG. 1 is a perspective view of the laboratory organizational unit of the present invention.

Referring now to the drawings, in which similar or corresponding parts are identified with the same reference numeral, and more particularly to FIG. 1, the laboratory organizer unit (LOU) of the present invention is designated generally at 10 and includes an enclosed housing 12 preferably supported on a plurality of wheels 14. Housing 12 includes forward and rearward ends 16 and 18, upper and lower ends 20 and 22, and opposing side walls 24 and 26.

Figure 2:
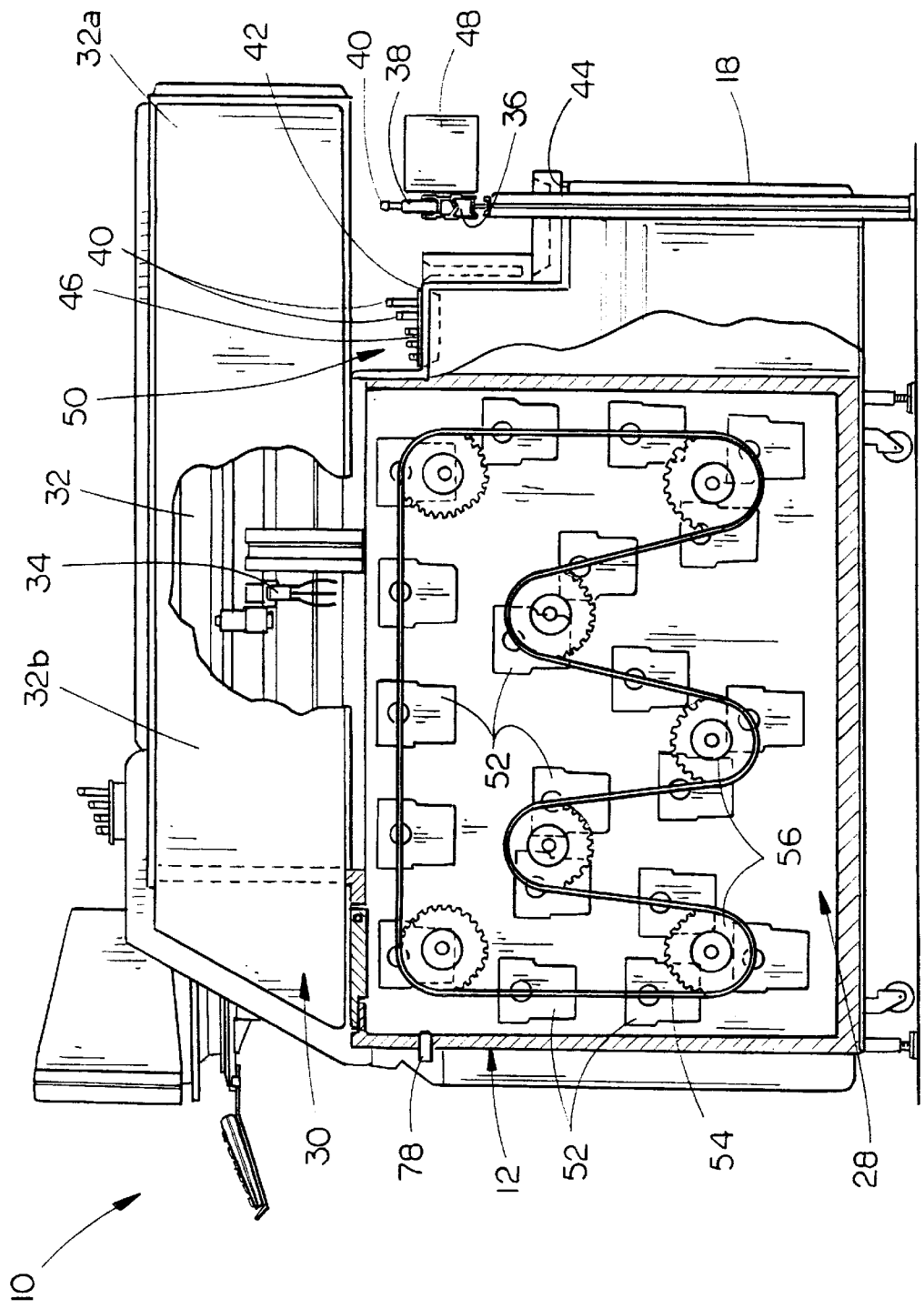
FIG. 2 is a side elevational view taken from the right side of the organizer unit, with portions broken away to show the interior thereof.

The lower portion of the interior of housing 12 defines a storage area 28, shown in FIG. 2, which is accessible from a specimen rack input/output (I/O) station 30, located in the upper portion of the forward end of housing 12, as well as by a robotic input/output unit (IOU) 32 extending rearwardly from a forward area 32b adjacent to the user station 30 in the upper end of the housing 12. The IOU 32 includes a robotic arm 34 which is operable over the top of storage area 28, as well as over a conveyor track 36 (which is not part of the LOU) extending outside the housing 12 of the LOU 10, beneath a rearward area 32a of IOU 32. Conveyor track 36 supports and conveys a plurality of individual specimen carriers 38, each specimen carrier 38 supporting a test tube 40 or other container thereon. Conveyor track 36 extends between various testing work stations and the LOU, to permit automated entry, testing, and storage of various specimens. While conveyor track 36 is shown located parallel to the rearward end 18 of LOU housing 12, the track may be located parallel either side wall 24 or side wall 26, so long as the IOU 32 extends over the top of the conveyor track 36.

As shown in FIG. 2, the rearward end 18 of housing 12 is stepped downwardly as it extends rearwardly to form a horizontal upper step 42 and a horizontal lower step 44. Conveyor track 36 extends over the lower step 44, as shown in FIGS. 1 and 2, with the upper edge of the conveyor track at substantially the same height as upper step 42. This permits the use of a specimen tube rack 46 on upper step 42 to receive and retain a plurality of test tubes 40 as a buffer between the conveyor track 36 and the storage area 28. An automated gate 48 is provided proximal to conveyor 36 to selectively stop a specimen carrier 38 under IOU 32 to permit the insertion or removal of a test tube 40 by robotic arm 34.

Rack 46 on upper step 42 serves as a buffer 50 to permit rapid insertion and retrieval of test tubes 40 from rack 46 to and from specimen carriers 38 as they travel on conveyor track 36. Storage area 28 of LOU 10 serves to store and archive large quantities of test tubes 40 and operates at a much slower speed. In this way, buffer 50 permits the conveyor track 36 to maintain its high rate of speed for transport of specimen carriers 38, while permitting the slow speed of the operation of storage and retrieval of test tubes from the storage area 28.

As shown in FIG. 2, a plurality of trays 52 are operably supported and moved between a pair of serpentine chains 54 (only one being shown in FIG. 2) engage around a plurality of cogs 56. The upper end of storage area 28 is open into the IOU 32, to permit robotic arm 34 to insert and retrieve test tubes from trays 52 as the trays are positioned along the upper end of storage area 28.

Figure 3:
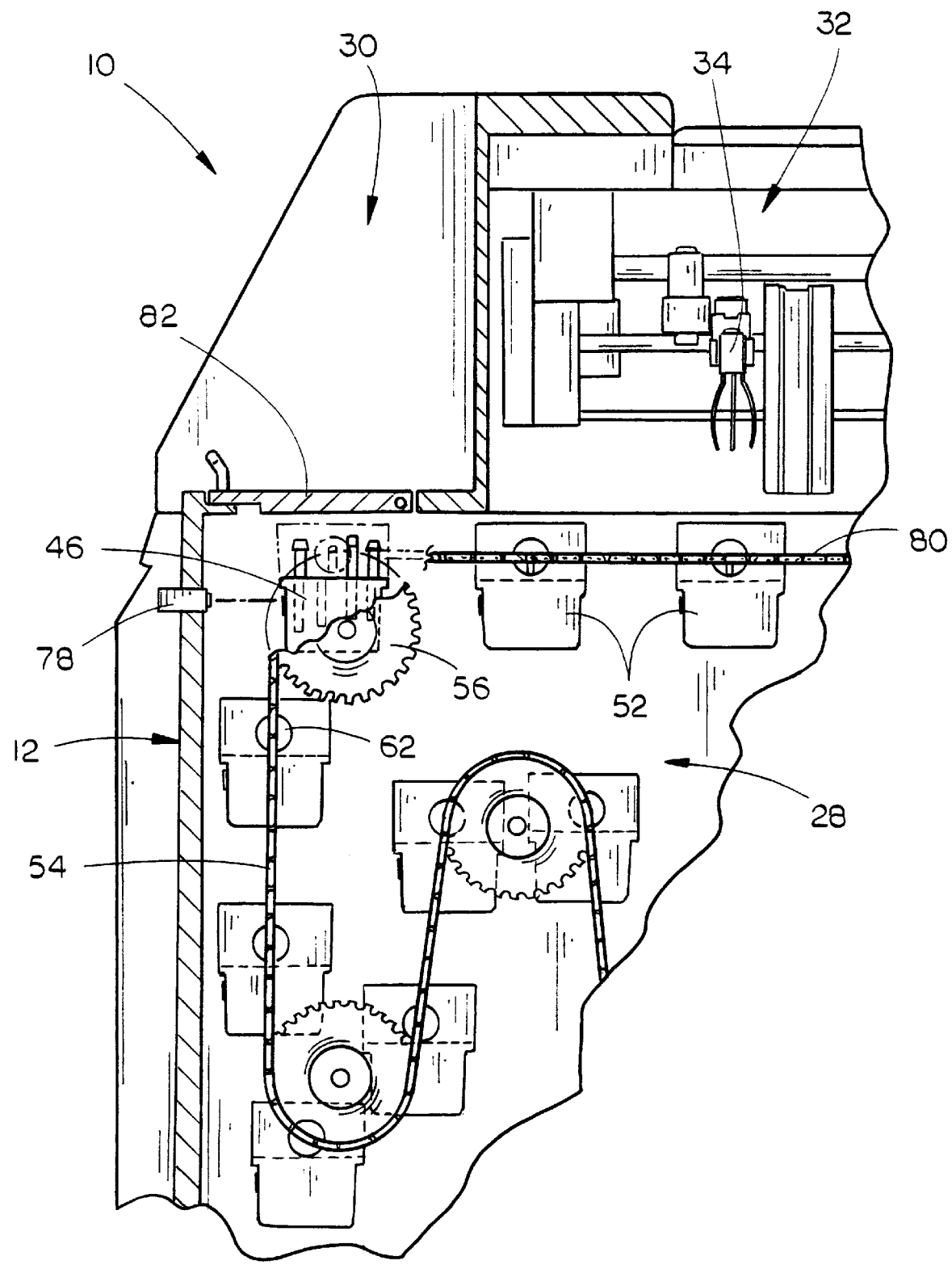
FIG. 3 is an enlarged partial sectional view through the organizer unit.
Figure 4:
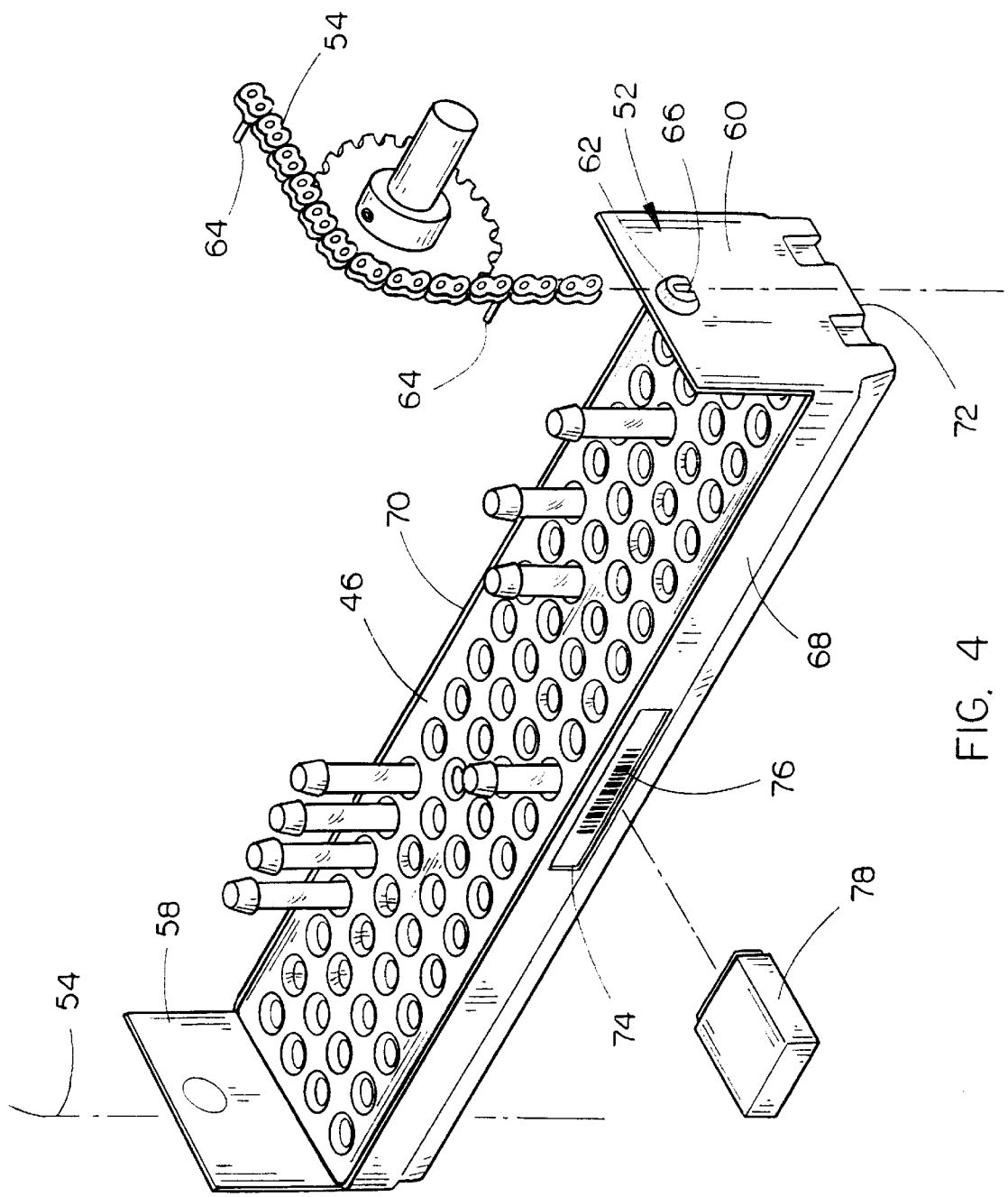
FIG. 4 is an enlarged pictorial view of one specimen container rack within the organizer unit.

Referring now to FIG. 4, one storage tray 52 is shown in greater detail. Tray 52 includes opposing upright ends 58 and 60, each end 58 and 60 having a projection 62 adjacent the upper end thereof for removable connection to the serpentine chains 54. As shown in FIG. 4, this connection could take the form of a projecting pin 64 on chain 54, with a receiver slot 66 formed in the projection. Thus, each tray 52 is suspended from a pair of opposing pins 64 between serpentine chains 54, to maintain the tray 52 in an upright position as it is moved through the serpentine pattern within the storage area 28, shown in FIG. 3. Each tray 52 includes forward and rearward vertical walls 68 and 70, as well as a bottom 72, to support a conventional specimen rack 46 therein. A cut-out 74 in forward wall 68 is provided generally centrally therein to reveal the bar code 76 imprinted on a label on the particular specimen rack 46. In this way, a bar code reader 78 can identify and locate a particular specimen rack 46 on a tray 52.

Referring now to FIG. 3, it can been seen that chains 54 and cogs 56 are arranged within storage area 28 to form a substantially horizontal flight 80 of chains 54 along the upper end of storage area 28. This permits access by robotic arm 34 from IOU 32 into the trays 52 which are supported along upper flight 80 in the open upper end of storage area 28.

The I/O station 30 in the forward upper end of housing 12 includes an access door 82 of the size to permit a specimen rack 46 to be inserted or retrieved from a tray 52 positioned under the access door 82. Bar code reader 78 is preferably mounted in housing 12 to read the bar code on the specimen rack 46 upon the insertion of the rack 46 into a tray 52 through access door 82.

Referring once again to FIG. 1, I/O station 30 also includes a keyboard 84 and monitor 86 to permit the input of information regarding a specimen rack, as well as operations of the LOU.

Figure 5:
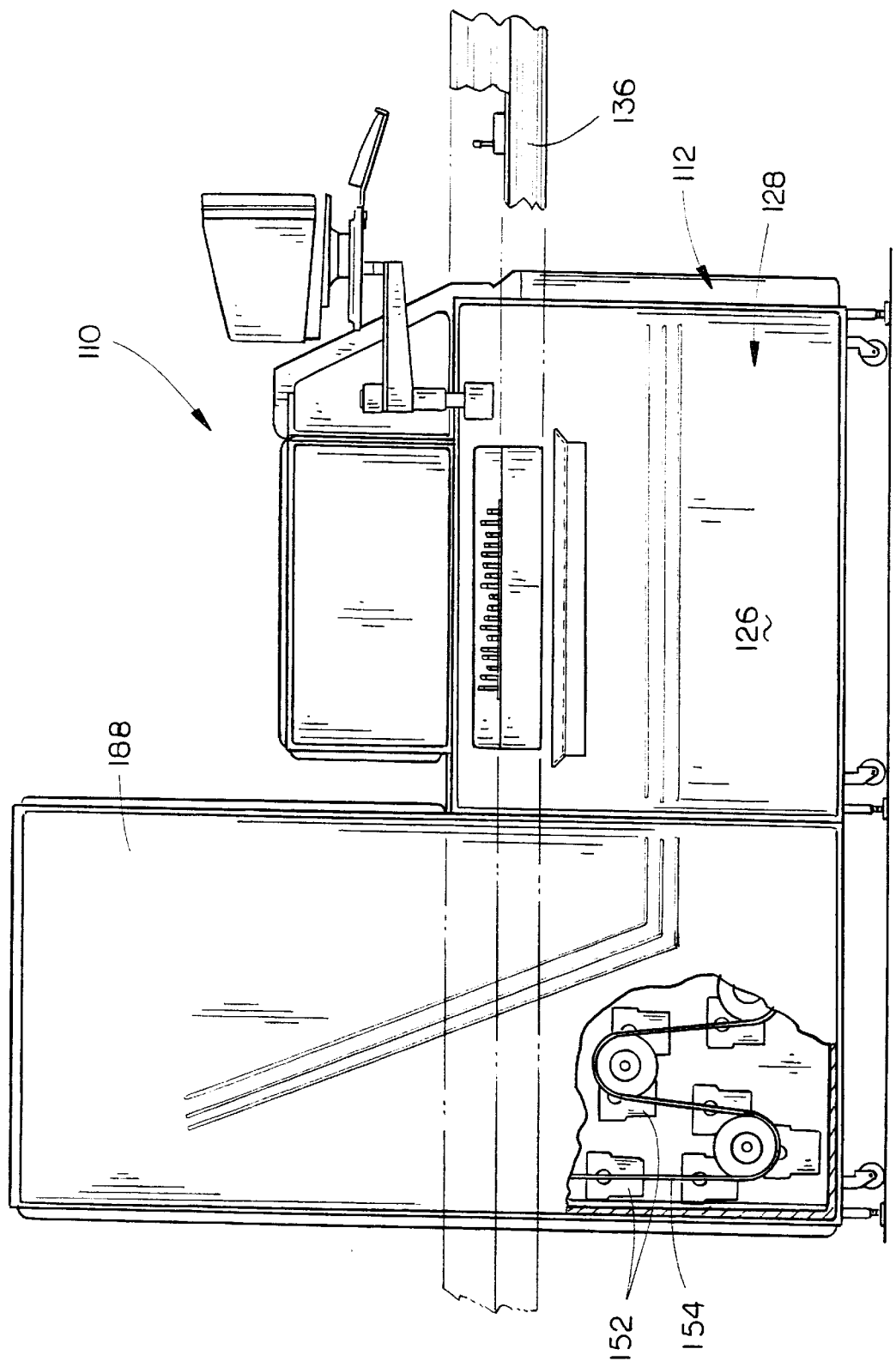
FIG. 5 is a side elevational view of a second embodiment of the laboratory organizer unit.

Referring now to FIG. 5, a second embodiment of the LOU is designated generally at 110 and is shown with a conveyor track 136 positioned along one side wall 126 of the housing 112, rather than adjacent the rearward end as in the first embodiment. The second embodiment of the LOU 110 includes a secondary storage unit 188 in operable communication with the storage area 128 of housing 112. This secondary storage unit 188 includes the same serpentine chains 154 and trays 152 as the main housing 112 and the preferred embodiment of the invention. Secondary storage unit 188 also permits the possibility of providing refrigerated storage if so desired.

Whereas the invention has been shown and described in connection with the preferred embodiments thereof, many modifications, substitutions and additions may be made which are within the intended broad scope of the appended claims.

We claim:

1. A laboratory organizer unit for inserting and retrieving specimen containers from a conveyor system, comprising:
   a housing having upper and lower ends, forward and rearward ends, and opposing sides;
   a storage area within the housing, including a rack for receiving and storing a plurality of vertically oriented specimen containers;
   a buffer area on the housing, including a rack for receiving and storing a plurality of vertically oriented specimen containers;
   a conveyor site for receiving a conveyor track in a predetermined position relative to the housing; and
   a transfer apparatus for selectively moving a specimen container between the storage area and buffer area and between the buffer area and the conveyor site.

2. The laboratory organizer unit of claim 1, wherein said organizer unit is electronically connected to a central processor for processing data relative to specimen containers being used by the organizer unit, and further comprising a user station on the housing, including a data input apparatus for inputting data to the central processor relative to racks inserted in the storage area.

3. The organizer unit of claim 2, wherein said transfer apparatus includes a robotic arm electronically connected to the central processor and operable to move vertically and horizontally to transfer specimen containers among the storage area, buffer area, and conveyor site.

4. The organizer unit of claim 3, wherein said storage unit includes a plurality of separate racks, each rack having means for receiving and retaining a plurality of specimen containers in upright positions.

5. The organizer unit of claim 4, wherein each storage area rack is supported on a tray, each tray being operably mounted on a continuous loop chain for selective movement within the storage area.

6. The organizer unit of claim 5, wherein said storage area is enclosed within said housing, including opposing forward and rearward ends, a bottom, opposing sides, and an open upper end permitting access to specimen containers in at least one of said racks.

7. The organizer unit of claim 6, wherein said continuous loop chain has a portion formed in a serpentine pattern, such that the trays are moved through a central portion of the storage area in addition to movement along the ends and sides of the storage area.

8. The organizer unit of claim 7, wherein each rack includes an identification code therein, and further comprising a reader mounted on the housing and connected to the central processor, for reading each identification code as the racks move within the storage area.

9. The organizer unit of claim 8, wherein the user station includes an operable access door in the housing permitting selective access to the storage area and at least one tray within the storage area.

10. The organizer unit of claim 1, wherein said storage unit includes a plurality of separate racks, each rack having means for receiving and retaining a plurality of specimen containers in upright positions.

11. The organizer unit of claim 10, wherein each storage area rack is supported on a tray, each tray being operably mounted on a continuous loop chain for selective movement within the storage area.

12. The organizer unit of claim 11, wherein said storage area is enclosed within said housing, including opposing forward and rearward ends, a bottom, opposing sides, and an open upper end permitting access to specimen containers in at least one of said racks.

13. The organizer unit of claim 12, wherein said continuous loop chain has a portion formed in a serpentine pattern, such that the trays are moved through a central portion of the storage area in addition to movement along the ends and sides of the storage area.

14. The organizer unit of claim 13, wherein each rack includes an identification code therein, and further comprising a reader mounted on the housing and connected to the central processor, for reading each identification code as the racks move within the storage area.

15. The organizer unit of claim 14, wherein said continuous loop chain has a portion formed in a serpentine pattern, such that the trays are moved through a central portion of the storage area in addition to movement along the ends and sides of the storage area.

16. The organizer unit of claim 11, wherein each rack includes an identification code therein, and further comprising a reader mounted on the housing and connected to the central processor, for reading each identification code as the racks move within the storage area.

17. The organizer unit of claim 11, wherein the user station includes an operable access door in the housing permitting selective access to the storage area and at least one tray within the storage area.

* * * * *